United States Patent
Krumbholz

(10) Patent No.: US 7,297,645 B2
(45) Date of Patent: Nov. 20, 2007

(54) OPALESCENT GLASS-CERAMIC PRODUCT

(75) Inventor: Klaus Krumbholz, Langen (DE)

(73) Assignee: Degudent GmbH, Hanau (DE)

( * ) Notice: Subject to any disclaimer, the term of this patent is extended or adjusted under 35 U.S.C. 154(b) by 169 days.

(21) Appl. No.: 10/500,475

(22) PCT Filed: Jun. 24, 2003

(86) PCT No.: PCT/EP03/06644

§ 371 (c)(1),
(2), (4) Date: Jul. 16, 2004

(87) PCT Pub. No.: WO04/000743

PCT Pub. Date: Dec. 31, 2003

(65) Prior Publication Data

US 2005/0155518 A1     Jul. 21, 2005

(30) Foreign Application Priority Data

Jun. 25, 2002 (DE) ................................ 102 28 381

(51) Int. Cl.
*C03C 3/097* (2006.01)
*C03C 4/00* (2006.01)
*A61K 6/06* (2006.01)

(52) U.S. Cl. .................. 501/2; 501/4; 501/5; 501/6; 501/8; 501/10; 501/63; 501/64; 501/66; 501/68; 501/69; 501/70; 501/24; 106/35; 65/33.1

(58) Field of Classification Search ................ 106/35; 501/2, 4, 5, 6, 8, 10, 63, 64, 66, 68, 69, 70; 65/33.1

See application file for complete search history.

(56) References Cited

U.S. PATENT DOCUMENTS

| 5,432,130 | A |   | 7/1995  | Rheinberger et al. |
| 5,702,514 | A | * | 12/1997 | Petticrew ..................... 106/35 |
| 6,022,819 | A |   | 2/2000  | Kaiser et al. |
| 6,120,591 | A | * | 9/2000  | Brodkin et al. ............... 106/35 |
| 6,200,137 | B1 | * | 3/2001 | Holand et al. ........... 433/212.1 |
| 6,280,863 | B1 | * | 8/2001 | Frank et al. ................. 428/701 |

\* cited by examiner

*Primary Examiner*—C. Melissa Koslow
(74) *Attorney, Agent, or Firm*—Dennison, Schultz & MacDonald

(57) ABSTRACT

An opalescent glass-ceramic product, especially for use as a dental material or as an additive to or component of dental material, including $SiO_2$, $Al_2O_3$, $P_2O_5$, $Na_2O$, $K_2O$, CaO and $Me(IV)O_2$. In order to obtain improved opalescence with improved transparency, in addition to fluorescence, thermal expansion and a combustion temperature adapted to other materials, the opalescent ceramic product is completely or substantially devoid of $ZrO_2$ and $TiO_2$, such that the Me(II)O content in the glass ceramic is less than approximately 4 wt % and the $Me(IV)O_2$ content amounts to approximately 0.5-3 wt %. The invention also relates to a method for the production of the opalescent glass-ceramic product.

15 Claims, No Drawings

OPALESCENT GLASS-CERAMIC PRODUCT

This application is a filing under 35 USC 371 of PCT/EP2003/006644, filed Jun. 24, 2003.

The invention relates to an opalescent glass ceramic, in particular an opalescent glass ceramic as a dental material or as an additive to or component of dental material, comprising at least the components $SiO_2$, $Al_2O_3$, $P_2O_5$, $Na_2O$, $K_2O$, CaO and $Me(IV)O_2$. Furthermore, the invention relates to a method for producing an opalescent glass ceramic as well as to the use of such a ceramic.

Opalescent glasses are known, for example, from EP 0 622 342 B1. EP 0 622 342 B1 discloses an opalescent glass based on $SiO_2$—$B_2O_3$—$Al_2O_3$—$K_2O$—$Na_2O$—CaO—BaO—SrO—$TiO_2$—$ZrO_2$—$P_2O_5$—$CeO_2$. The linear thermal expansion coefficients (TEC) therein are either much too high (Examples 5, 15, 26, 27 with TEC≧15.1) or much too low (TEC≦10.8) to be usable for the preferred use of the material as a veneer ceramic for metal tooth restoration in pure form. To coat current alloys, a blending with further glasses is required.

Moreover, tests have shown that the glass ceramic products known from EP 0 622 342 B1 are too dull, so that a good aesthetic appearance is not ensured. Overall, the opalescent glass ceramic products known from EP 0 622 342 B1 exhibit a too weak and only slightly bake-stable opalescence, and a too high opacity and have no fluorescence.

A porcelain material intended for the dental field is known from U.S. Pat. No. 6,022,819. It has $TiO_2$ or $ZrO_2$ as components. The $SiO_2$ content is preferably 50 to 85% by weight.

The object of the present invention is to make available an opalescent glass ceramic product, a method for producing same as well as its use, which has improved opalescence with simultaneously improved transparency and a baking temperature or thermal expansion coefficients adapted to other materials as well as fluorescence.

According to the invention, the object is essentially achieved by an opalescent glass ceramic product of the aforementioned type in which the opalescent glass ceramic is devoid of $ZrO_2$ and $TiO_2$, the glass ceramic product has a Me(II)O content of less than 4% by weight and the Me(IV)$O_2$% by weight is from 0.5 to about 3% by weight. Preferably, it is provided that the $Me(IV)O_2$ content is composed of 0-1% by weight $CeO_2$ and O—2.5% by weight $SnO_2$.

In particular, the Me(II)O content is 2-3.5% by weight, preferably 2.5-3% by weight.

A preferred composition contains the following components:

| Component | % by weight |
|---|---|
| $SiO_2$ | 55-62 |
| $Al_2O_3$ | 13-17 |
| $B_2O_3$ | 0-2 |
| $P_2O_5$ | 1.5-3 |
| $Li_2O$ | 0-2 |
| $Na_2O$ | 7-12 |
| $K_2O$ | 8-12 |
| MgO | 0-2 |
| CaO | 1-≦4 |
| BaO | 0-2 |
| $Tb_2O_3$ | 0-3 |
| $Me(IV)O_2$ | 0.5-3 | the indicated amount of $Me(IV)O_2$ being composed of 0-1% by weight of $CeO_2$ and 0-2.5% by weight $SnO_2$.

In particular, the composition of the glass ceramic is distinguished by:

| Component | % by weight |
|---|---|
| $SiO_2$ | 58-60 |
| $Al_2O_3$ | 14-15 |
| $P_2O_5$ | 2.3-2.6 |
| $Na_2O$ | 9.5-10.5 |
| $K_2O$ | 9-10 |
| CaO | 2.8-3.0 |
| $SnO_2$ | 1.3-1.6 |
| $CeO_2$ | 0.3-0.4 |
| $Tb_2O_3$ | 0-2.0 |

According to the invention, an improved opalescence is obtained by demixing of the glasses based on $P_2O_5$ and $SnO_2$ contents. The thermal expansion coefficient (TEC) of the ceramic according to the invention is in the range of 9.0-13.5×10$^{-6}$/K and can be controlled by the $K_2O$ content.

By additionally fusing $CeO_2$ and/or $Tb_2O_3$, it can be attained that the glass ceramic fluoresces, a desirable property for dental ceramics. A strong, neutral fluorescence is obtained by combining both oxides.

Furthermore, the applicable baking temperature of the ceramic can be controlled by the portion of $B_2O_3$, $Li_2O$ and $Na_2O$ and adapted to desired values. The applicable relevant baking temperature of the ceramics according to the invention are in the range of 870 to 970° C.

On the whole, a glass ceramic is provided which satisfies all requirements with regard to aesthetic coating ceramics.

A method for producing the glass ceramic according to the invention is characterized by the following procedural steps:

1) weighing in the components;
2) preferably mixing the mixture in a gyro mixer;
3) melting the mixture in a preferably gas-heated furnace such as a drip-feed crucible furnace, preferably at about 1500° C.;
4) quenching the molten mass coming out of the furnace in a water bath and subsequent drying;
5) short grinding of the frit thus obtained in a mill (e.g. ball mill);
6) tempering the frit;
7) after drying, filling the frit in a mill, such as a ball mill, and grinding, preferably to about 10000 revolutions;
8) sifting the ground frit through a sieve, the sieve opening forming the end.

Preferably, the frit is tempered in the following manner:
a. stacking the ground frits on quartz-coated fire-clay plates,
b. placing the fire-clay plates in a furnace (e.g. electric furnace) heated to about 850-1000° C., and preferably 960° C.
c. removing the plates from the furnace after about 30-60 minutes, preferably 40 minutes,
d. quenching the fused frit cakes in a water bath.

The ground frit is preferably sifted through a sieve having a mesh size M in the range of 80 μm≦M≦120 μm, preferably M=100 μm.

Unlike the glass ceramic known from EP 0 622 342 B1, the glass ceramic according to the invention needs no $ZrO_2$ and $TiO_2$ and the Me (II)O content remains less than 3% by weight. Moreover, by melting in $CeO_2$ and $Tb_2O_3$, the opal ceramic of the invention exhibits fluorescence. Furthermore, the baking temperature can be adapted to the desired application. The thermal expansion can be set by selective leucite crystallization in the ceramic according to the invention in such a way that it can be used especially for coating metal frame materials.

Further details, advantages and features of the invention can be found in the preferred embodiments in the following description.

The invention will be described with reference to the following embodiments, wherein the Tests 1, 2, 8 to 21 are preferred and Tests 11 and 13 especially preferred. The compositions of the opal ceramic can be found in Table 1.

TABLE I

| Test | Ivo. 15 | 1 | 2 | 3 | 4 | 5 | 6 | 7 | 8 | 9 | 10 | 11 | 12 |
|---|---|---|---|---|---|---|---|---|---|---|---|---|---|
| | | | | | % by weight | | | | | | | | |
| SiO2 | 55.34 | 59.78 | 59.05 | 60.01 | 58.03 | 56.22 | 59.83 | 55.53 | 58.44 | 58.93 | 58.02 | 59.08 | 58.72 |
| Al2O3 | 16.09 | 14.52 | 14.63 | 16.45 | 15.91 | 16.83 | 16.4 | 14.71 | 14.23 | 14.44 | 14.34 | 14.48 | 14.78 |
| B2O3 | 0.22 | 0.44 | 0.44 | | | 1.09 | 1.07 | 2.23 | 0.44 | | 1.1 | | |
| P2O5 | 2.59 | 2.32 | 2.42 | 2.33 | 2.38 | 2.06 | 1.4 | 2.46 | 2.44 | 2.43 | 2.43 | 2.43 | 2.44 |
| Li2O | | | | 1.28 | 1.31 | 1.1 | 1.29 | 0.45 | | | | | |
| Na2O | 9.08 | 9.36 | 9.3 | 4.44 | 6.39 | 5.91 | 6 | 9.97 | 9.84 | 10.03 | 10.01 | 10.04 | 9.13 |
| K2O | 11.88 | 9.09 | 9.23 | 13.49 | 12.96 | 13.11 | 12.86 | 10 | 9.63 | 9.21 | 9.15 | 9.24 | 10.19 |
| MgO | | | | | | | | | | | | | |
| CaO | 2.6 | 2.97 | 2.95 | 0.09 | 1.3 | 1.91 | 0.09 | 2.88 | 2.98 | 2.97 | 2.97 | 2.97 | 2.97 |
| BaO | | | | | | | | | | | | | |
| Tb2O3 | | | | | | | | | | | | | |
| SnO2 | | 1.52 | 0.88 | 0.85 | 0.86 | 0.87 | | 1.45 | 0.89 | 0.88 | 0.88 | 1.43 | 1.44 |
| CeO2 | | | 1.1 | 1.06 | 0.86 | 0.87 | 1.07 | 0.33 | 1.11 | 1.1 | 1.1 | 0.33 | 0.33 |
| ZrO2 | 1.9 | | | | | | | | | | | | |
| TiO2 | 0.3 | | | | | | | | | | | | |
| | | | | Calculated thermal expansion coefficient (Alpha ×10 exp. −6/K) | | | | | | | | | |
| | 10.73 | 9.91 | 9.98 | 9.64 | 10.53 | 10.23 | 9.96 | 10.58 | 10.35 | 10.31 | 10.02 | 10.32 | 10.28 |
| | | | | Applicable relevant baking temperature in ° C. | | | | | | | | | |
| | 960 | 940 | 940 | 980 | 920 | 940 | 940 | 870 | 920 | 940 | 920 | 940 | 950 |
| | | | | Tempering of the glass frit (Min./° C.) | | | | | | | | | |
| | 60/950 | 30/950 | 30/950 | | 30/950 | | 30/950 | 30/980 | 30/930 | 30/960 | 30/940 | 60/950 | 40/960 |
| | | | | Measured thermal expansion coefficient | | | | | | | | | |
| | unknown | unknown | 9.71 | unknown | | 17 | unknown | 12.01 | unknown | unknown | unknown | 11.08 | 12.8 |
| | | | | | Optical values | | | | | | | | |
| L*tran | 69.7 | 77.1 | 76.6 | cloudy | | 81.4 | 65.8 | 79.8 | 80.5 | 80.9 | 81 | 79 | |
| b*trans. | 26.5 | 31.6 | 32.8 | | | 9.4 | 27.4 | 25.6 | 29.3 | 34.9 | 30.3 | 32.9 | |
| b*ref | | | | | | | | | | | | | |

| Test | 13 | 13 Zr/Ti | 14 | 15 | 16 | 17 | 18 | 19 | 20 | 21 | 22 |
|---|---|---|---|---|---|---|---|---|---|---|---|
| | | | | | % by weight | | | | | | |
| SiO2 | 58.48 | 58.48 | 57.19 | 58.97 | 58.1 | 57.19 | 57.67 | 57.86 | 57.86 | 58.22 | 58.22 |
| Al2O3 | 14.61 | 14.61 | 14.31 | 14.66 | 14.51 | 14.31 | 14.41 | 14.43 | 14.43 | 14.62 | 14.7 |
| B2O3 | | | | | | | | | | | |
| P2O5 | 2.44 | 2.44 | 2.44 | 2.04 | 2.85 | 2.44 | 2.44 | 2.44 | 2.44 | 2.46 | 2.51 |
| Li2O | | | | | | | | | | | 0.67 |
| Na2O | 9.9 | 9.9 | 9.85 | 9.91 | 9.88 | 9.85 | 9.86 | 9.87 | 9.87 | 9.19 | 9.21 |
| K2O | 9.93 | 9.93 | 9.79 | 9.8 | 10.03 | 9.79 | 9.82 | 9.86 | 9.86 | 10.94 | 10.1 |
| MgO | | | | | | | | | | | 1.43 |
| CaO | 2.86 | 2.86 | 2.67 | 2.86 | 2.86 | 2.67 | 2.67 | 2.67 | 2.67 | 2.83 | 0.07 |
| BaO | | | | | | | | | | | 1.3 |
| Tb2O3 | | | 1.99 | | | 1.99 | 1.99 | 1.99 | 1.99 | | |
| SnO2 | 1.44 | | 1.44 | 1.44 | 1.44 | 1.77 | 0.88 | 0.44 | | 1.42 | 1.45 |
| CeO2 | 0.33 | | 0.33 | 0.33 | 0.33 | | 0.22 | 0.44 | 0.88 | 0.33 | 0.33 |
| ZrO2 | | 1.22 | | | | | | | | | |
| TiO2 | | 0.55 | | | | | | | | | |
| | | | | Calculated Thermal Expansion coefficient (Alpha ×10 exp. −6) | | | | | | | |
| | 10.49 | 10.45 | 10.52 | 10.41 | 10.56 | 10.52 | 10.54 | 10.54 | 10.54 | 10.55 | 10.44 |
| | | | | Applicable relevant baking temperature in ° C. | | | | | | | |
| | 950 | 950 | 960 | 950 | 950 | 950 | 950 | 950 | 950 | 950 | 930 |
| | | | | Tempering of the glass frit *(Min./° C.) | | | | | | | |
| | 40 | 40/960 | 40/960 | 40/960 | 40/960 | 40/960 | 40/960 | 40/960 | 40/960 | 40/960 | 40/940 |
| | | | | Measured thermal expansion coefficient | | | | | | | |
| | 12.6 | 10.59 | 11.5 | 11.24 | 11.08 | 10.53 | unknown | unknown | 12.34 | 13.23 | unknown. |
| | | | | Optical values | | | | | | | |
| L*trans | 80 | 78.9 | 80.3 | 83.3 | 78.1 | 82.6 | 79.5 | 80.2 | 75.2 | 76 | 71.3 |
| b*trans | 32.9 | 33.6 | 27.6 | 24.4 | 36.1 | 28.5 | 32.5 | 31 | 33.2 | 33.8 | 15.2 |
| b*ref | | | | | | | | | | | |

A comparison of the tests shows that the thermal expansion coefficient of the glass ceramic according to the invention is controllable. Thus, a thermal expansion coefficient (TEC) in the range of 9.0 to $13.5 \times 10^{-6}$, preferably 10.5 to $12 \times 10^{-6}$, can be set. In comparison to the ceramics known from EP 0 622 342 B1, which have either too low a TEC ($\leq 11 \times 10^{-6}$/K) or a too high TEC ($\geq 16 \times 10^{-6}$/K), the glass ceramic according to the invention can be set in the TEC range of 11.0 to $13.0 \times 10^{-6}$/K for coating ceramics, which is especially important in the dental field.

Tests have shown that the $SnO_2$- and/or $CeO_2$-content is suitable for stimulating the crystallization of small amounts of leucite which are required for increasing the TEC.

A comparison of Test 13 with 1.44% $SnO_2$ with a Test in which the $SnO_2$ was replaced by $ZrO_2$ and $TiO_2$ according to the claims of EP 0 622 342 B1 (Test "13 Zr/Ti" in the Table), clearly shows that, in the latter Test, the TEC corresponds approximately to the mathematically determined value, assuming a homogeneous glass, which can indicate the lack of a leucite crystallization.

The examples show that the TEC in the glass ceramic of the invention can be controlled by the $K_2O$ content when there is a sufficient $Al_2O_3$ content. In particular, Tests 11 to 14 and 21 show this property. Tests 15 and 16 indicate that the $P_2O_5$ content, which determines the extent of the phase separation of the glass, also has an effect.

By additionally fusing in $CeO_2$ and/or $Tb_2O_3$, the glass ceramic can be caused to fluoresce. It could thereby be ascertained that fusing in only $CeO_2$ results in weak bluish fluorescence and $Tb_2O_2$ in a stronger yellow fluorescence which is not typical for natural teeth. A strong, neutral fluorescence is only obtained with a combination of both oxides, as Tests 17 to 20 show. The Tests 19 and 20 are optimal for fluorescence.

The baking temperature of the glass ceramic can be controlled by the proportion of $B_2O_3$, $Li_2O$ and $Na_2O$ and adapted to the desired value, as Tests 10 and 12 show. The applicable relevant baking temperatures of the glass ceramics according to the invention are in the range of 870° C. to 970° C.

Test 13 has all of the preferred properties. The baking temperature and the TEC are ideal and, at the same time, the optical values with a transparency of L* (Transparency)=80 and a Δb*=32.9 are very good. In comparison thereto, the ceramic (Ivo. 15) prepared according to EP 0 622 342 B1 only has a Δb* of 26.5 at a transparency of L* (transp.)= 69.7.

It should be noted that the chemical stability and bending strength of the illustrated examples meet the requirements of the relevant standards for dental ceramics (ISO 9693).

The exemplary embodiments according to Tests 13, 15 and 16 show the effect of the $P_2O_5$ content. Example 13 with a $P_2O_3$ content of 2.44% by weight is considered optimal, while the transparency is increased at the expense of opalescence in Example 15 with a $P_2O_5$ content of 2.04% by weight and an increased opalescence with reduced transparency can be ascertained in Example 16 with a $P_2O_5$ content of 2.85% by weight.

Table 1 also shows embodiments (Tests 3, 4, 5, 6, 7 and 22) whose compositions are outside of the claimed range. In this case, Tests 3 to 5 have a too high $K_2O$ content and additionally Test 3 has too little CaO. It has been found shown that these exemplary embodiments are already too dull in the untempered state, presumably due to a too strong leucite crystallization. In spite of a too high leucite content, Test 6 is transparent since it only has a slight tendency to demix due to a $P_2O_5$ content of less than 1.5% by weight, but its opalescence is too low. In Test 7, a too high $B_2O_3$ content results in a strong dullness and, in Test 22, CaO was replaced by MgO nd BaO which resulted in a reduced opalescence.

The glass ceramics according to the invention were produced according to the following method:
1. Weighing in the raw materials as noted in Table 1.
2. Mixing the mixture in a gyro mixer.
3. Melting the mixture in a gas-heated drip-feed crucible furnace at about 1500° C.
4. Quenching the molten mass running out of the furnace in a water bath.
5. Drying the molten mass.
6. Brief grinding of the frit thus obtained in a ball mill.
7. Tempering the frit in the following manner:
   stacking the ground frits on quartz-coated fire-clay plates
   placing these plates in an electric furnace heated to 960° C.
   removing the plates from the furnace after about 40 minutes
   quenching the fused frit cakes in the water bath.
8. After drying, filling the frit into the ball mill and grinding, preferably to about 10,000 revolutions.
9. Sifting the ground frits through a sieve, preferably having 100 μm mesh size.

To measure opalescence and transparency of the opal ceramic, it should be noted that 3 grams of the powdery opal ceramics were compacted in a press to form a round blank and these were sintered together in a dental vacuum baking furnace at the same temperature as in Test 13 of 950° C. The round blank thus obtained has a thickness of about 2.5 mm. In the case of opalescence, these round blanks appear orange/yellow with transmitted light since the unscattered long-wave light catches the eye. On the other hand, when looking at it against a dark background, the round blank appears bluish, since the more strongly scattered short-wave light is seen in this case.

This phenomenon can be determined quantitatively with a spectrophotometer. For this purpose, the L*, a*, b* values were measured in transmission and in reflection on a black base in the photometer of, for example, the Minolta corporation (CM-3610d), whereby a 2° observer and standard light D65 are required. In the L*, a*, b* colour system, a positive b* value represents the yellow part of the light, on the other hand, a negative b* value represents its blue part. The higher the absolute amount, the more intense the colour.

Accordingly, the opalescent round blanks thus produce positive b* values during transmission and negative b* values during reflection. The more the two b* values deviate from one another, the strong the opalescence.

Moreover, the L* value measured in transmission can be used as a measure for the transparency of the round blank.

Aesthetically satisfying results in dental restoration are obtained with opal ceramics whose round blanks have a Δb* of at least 25 and L* (transm.) of at least 75.

The invention claimed is:

1. An opalescent glass ceramic which is devoid of $ZrO_2$ and $TiO_2$, and which comprises an Me(II)O component in an amount of less than 4% by weight, and an Me(IV)$O_2$ component in an amount of 0.5 to 3% by weight, the glass ceramic consisting essentially of:

| Component | % by weight |
| --- | --- |
| $SiO_2$ | 55-62 |
| $Al_2O_3$ | 13≦-17 |
| $B_2O_3$ | 0-2 |
| $P_2O_5$ | 1.5-3 |
| $Li_2O$ | 0-2 |
| $Na_2O$ | 7-12 |
| $K_2O$ | 8-12 |
| MgO | 0-2 |

-continued

| Component | % by weight |
|---|---|
| CaO | 1-<4 |
| BaO | 0-2 |
| $Tb_2O_3$ | 0-3 |
| $Me(IV)O_2$ | 0.5-3 | wherein said $Me(IV)O_2$ consists essentially of $0<CeO_2 \leq 1$ and $0<SnO_2 \leq 2.5$, and wherein the glass ceramic has a thermal expansion coefficient (TEC) in the range of $9.0\text{-}13.5\times10^{-6}/K$.

2. The opalescent glass ceramic according to claim 1, wherein Me(II)O is present in an amount of 23.5% by weight.

3. The opalescent glass ceramic according to claim 1, having a composition of:

| Component | % by weight |
|---|---|
| $SiO_2$ | 58-60 |
| $Al_2O_3$ | 14-15 |
| $P_2O_5$ | 2.3-2.6 |
| $Na_2O$ | 9.5-10.5 |
| $K_2O$ | 9-10 |
| CaO | 2.8-3 |
| $Tb_2O_3$ | 0-2 |
| $CeO_2$ | 0.3-0.4 |
| $SnO_2$ | 1.3-1.6. |

4. The opalescent glass ceramic according to claim 1, which is a dental material or an additive for a dental material.

5. The opalescent glass ceramic according to claim 1, wherein the thermal expansion coefficient (TEC) is in the range of $10.5\text{-}12.0\times10^{-6}/K$.

6. A method for producing an opalescent glass ceramic which is devoid of $ZrO_2$ and $TiO_2$, which has a thermal expansion coefficient (TEC) in the range of $9.0\text{-}13.5\times10^{-6}/K$, and which comprises an Me(II)O component in an amount of less than 4% by weight and an $Me(IV)O_2$ component in an amount of 0.5 to 3% by weight, comprising the steps of:

mixing together components consisting essentially of:

| Component | % by weight |
|---|---|
| $SiO_2$ | 55-62 |
| $Al_2O_3$ | $13 \leq -17$ |
| $B_2O_3$ | 0-2 |
| $P_2O_5$ | 1.5-3 |

| Component | % by weight |
|---|---|
| $Li_2O$ | 0-2 |
| $Na_2O$ | 7-12 |
| $K_2O$ | 8-12 |
| MgO | 0-2 |
| CaO | 1-<4 |
| BaO | 0-2 |
| $Tb_2O_3$ | 0-3 |
| $Me(IV)O_2$ | 0.5-3 | wherein said $Me(IV)O_2$ consists essentially of $0<CeO_2 \leq 1$ and $0<SnO_2 \leq 2.5$, melting the mixture in a furnace;

quenching the molten mass from the furnace in a water bath and drying to form a frit;

grinding the frit in a mill;

tempering the ground frit;

drying the tempered frit, and filling the frit in a ball mill and grinding, and sifting the ground frit through a sieve.

7. The method according to claim 6, wherein the tempering of the frit comprises the steps of:

stacking the ground frit on quartz-coated fire-clay plates, placing the fire-proof plates in a furnace heated to a temperature T with $850°\ C. \leq T \leq 1000°\ C.$, thereby fusing the ground frit, removing the plates from the furnace after a time t with $30\ min \leq t \leq 60\ min$, and quenching the fused frit in a water bath.

8. The method according to claim 6, wherein the components are mixed in a gyro mixer.

9. The method according to claim 6, wherein the mixture is melted in a gas-heated drip-feed crucible furnace.

10. The method according to claim 6, wherein the filling and grinding step comprises filling the frit into a ball mill and grinding at about 10,000 revolutions per minute.

11. The method according to claim 6, wherein the ground frit is sifted through a sieve having a mesh size M in the range of $80\ \mu m \leq M \leq 120\ \mu m$.

12. The method according to claim 7, wherein the ground frit is fused at a temperature of 870 to 970° C.

13. The method according to claim 6, wherein the thermal expansion coefficient is set to $9.0\text{-}13.5\times10^{-6}/K$ by adjusting the $K_2O$ content.

14. The method according to claim 6, wherein the melting temperature of the opalescent glass ceramic is controlled to 870° C. to 970° C.

15. The method according to claim 6, wherein % by weight $Al_2O_3$ is 14-17.

* * * * *

UNITED STATES PATENT AND TRADEMARK OFFICE
CERTIFICATE OF CORRECTION

PATENT NO. : 7,297,645 B2
APPLICATION NO. : 10/500475
DATED : November 20, 2007
INVENTOR(S) : Klaus Krumbholz Page 1 of 1

It is certified that error appears in the above-identified patent and that said Letters Patent is hereby corrected as shown below:

Col. 7, line 15, Claim 2, change "23.5%" to: "2-3.5%".

Signed and Sealed this
Twenty-seventh Day of November, 2012

David J. Kappos
*Director of the United States Patent and Trademark Office*